United States Patent
Robinson et al.

(10) Patent No.: US 12,076,218 B2
(45) Date of Patent: Sep. 3, 2024

(54) DEVICES, SYSTEMS, AND METHODS FOR INSTILLATION OF FOAMED FLUID WITH NEGATIVE PRESSURE WOUND THERAPY

(71) Applicant: Solventum Intellectual Properties Company, Maplewood, MN (US)

(72) Inventors: Timothy Mark Robinson, Shillingstone (GB); Joanna Perkins, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 775 days.

(21) Appl. No.: 17/148,088

(22) Filed: Jan. 13, 2021

(65) Prior Publication Data

US 2021/0128362 A1 May 6, 2021

Related U.S. Application Data

(60) Continuation of application No. 15/938,111, filed on Mar. 28, 2018, now Pat. No. 10,918,527, which is a division of application No. 13/009,630, filed on Jan. 19, 2011, now Pat. No. 9,974,693.

(60) Provisional application No. 61/297,471, filed on Jan. 22, 2010.

(51) Int. Cl.
*A61M 1/00* (2006.01)
*A61F 13/00* (2024.01)
*A61F 13/05* (2024.01)

(52) U.S. Cl.
CPC ............... *A61F 13/05* (2024.01); *A61M 1/92* (2021.05); *A61F 2013/00174* (2013.01); *A61F 2013/00412* (2013.01); *A61F 2013/00536* (2013.01); *A61F 2013/0054* (2013.01); *A61F 2013/0074* (2013.01); *A61F 2013/00825* (2013.01); *A61M 1/96* (2021.05); *A61M 1/982* (2021.05)

(58) Field of Classification Search
CPC ............ A61F 13/05; A61F 2013/00174; A61F 2013/00412; A61F 2013/00536; A61F 2013/0054; A61F 2013/0074; A61F 2013/00825; A61M 1/92; A61M 1/96; A61M 1/982
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Benjamin J Klein

(57) ABSTRACT

Systems and methods for delivering a foamed fluid to a wound of a patient (e.g., through a wound dressing covering the wound and coupled to the skin around the wound).

17 Claims, 3 Drawing Sheets

(56) References Cited

U.S. PATENT DOCUMENTS

| | | | |
|---|---|---|---|
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A * | 10/1989 | Austad ............... A61F 13/04 602/900 |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0142684 A1 * | 6/2006 | Shanbrom ............... A61L 15/44 602/41 |
| 2008/0114277 A1 * | 5/2008 | Ambrosio ............... A61P 17/02 602/53 |
| 2009/0157017 A1 * | 6/2009 | Ambrosio ........... A61M 35/006 514/1.1 |
| 2009/0246260 A1 * | 10/2009 | Delmotte ................ A61L 15/44 424/94.1 |
| 2010/0135915 A1 * | 6/2010 | Greener ............... A61K 31/196 424/43 |
| 2012/0078154 A1 * | 3/2012 | Pigg ..................... A61L 15/425 602/46 |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |

(56) References Cited

FOREIGN PATENT DOCUMENTS

| | | |
|---|---|---|
| JP | 4129536 B2 | 8/2008 |
| NO | 90/010424 A1 | 9/1990 |
| SG | 71559 | 4/2002 |
| WO | 80/02182 A1 | 10/1980 |
| WO | 87/04626 A1 | 8/1987 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp .: 66-70, and 9 page English translation thereof.

Yusupov. YU.N., et al; "Active Wound Drainage", Vestnki Khirurgi, vol. 138, Issue 4, 1987, and 7 page English translation thereof.

Davydov, YU.A., et al; "Bacteriological and Cytological Assessment of Vacuum Therapy for Purulent Wounds"; Vestnik Khirugi, Oct. 1988, pp. 48-52, and 8 page English translation thereof.

Davydov, YU.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al.; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

\* cited by examiner

DEVICES, SYSTEMS, AND METHODS FOR INSTILLATION OF FOAMED FLUID WITH NEGATIVE PRESSURE WOUND THERAPY

CROSS-REFERENCE TO RELATED APPLICATIONS

This application is a continuation of U.S. patent application Ser. No. 15/938,111, filed Mar. 28, 2018, which is a divisional of U.S. patent application Ser. No. 13/009,630, filed Jan. 19, 2011, now U.S. Pat. No. 9,974,693, which claims the benefit, under 35 USC 119(e), of the filing of U.S. Provisional Patent Application No. 61/297,471, entitled "Devices, Systems, and Methods for Instillation of Foamed Fluid with Negative Pressure Wound Therapy," filed Jan. 22, 2010, which are incorporated herein by reference for all purposes.

BACKGROUND

1. Field of the Invention

The present invention relates generally to healing of wounds and wound-treatment therapies. More particularly, but not by way of limitation, the present invention relates to systems and methods for improving fluid-instillation and negative pressure wound therapy (NPWT) apparatuses and methods.

2. Background Information

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue. The porous pad may be incorporated into a dressing having other components that facilitate treatment Typical instillation therapy instills fluid into a wound under a low positive pressure. For maximum therapeutic effect, the instilled fluid should reach all exposed tissue surfaces. The practice of fully filling a wound with instillation fluid, combined with the application of porous wound fillers and negative pressure to help distribute fluid, are techniques used to try an achieve good instillation therapy. Such techniques include numerous disadvantages. For example, filling a wound with fluid is wasteful, particularly where expensive fluids (e.g. antibiotics) are used as the bulk of the fluid enters the dressing (e.g., a foam) to enable the surface of the wound to be 'coated' with instillation fluid.

Even where the instilled fluid is inexpensive, large volumes of fluid may be involved, requiring frequent canister changes that may lead to user dissatisfaction. Although low positive pressures are typically used to fill the wound cavity, the hydraulic (essentially incompressible) nature of the fluid means that over filling can quickly cause drape leakage. Tortuous contours within a wound cavity may be difficult to reach with both foam dressings and liquid-fill techniques as gas pockets may be created. Applying a low vacuum during liquid instillation (to help maintain a seal and reduce leaking, to minimize patient discomfort, and to aid fluid distribution) can be problematic as instilled fluid may be removed before it is fully distributed through the dressing.

For at least the reasons described above, improved wound treatment systems and methods are therefore desired.

SUMMARY

The present disclosure includes embodiments of wound-treatment systems, wound fillers, and methods.

Some embodiments of the present wound-treatment apparatuses (e.g., for the treatment of wounds using negative pressure wound therapy) comprise: a drape for securing to the skin of a patient around a wound, thereby creating a space between the wound and the drape; a vacuum source in fluid communication with the space between the wound and the drape for applying a negative pressure to that space; and a source of foamed fluid in fluid communication with the space between the wound and the drape for applying the foamed fluid to the wound. Some embodiments further comprise a wound filler for positioning on the wound in the space between the wound and the drape. In some embodiments, the source of foamed fluid generates the foamed fluid by mixing first and second fluids (e.g., liquids). In some embodiments, the mixing is performed by combining the first and second fluids in a single conduit. In some embodiments, the mixing is performed by combining the first and second fluids in the space between the wound and the drape. In some embodiments, the first fluid (e.g., liquid) is an acidic solution and the second fluid (e.g., liquid) is a basic solution. In some embodiments, the first fluid (e.g., liquid) comprises at least one of citric acid, acetic acid, hypochlorous acid, ascorbic acid, and benzoic acid. In some embodiments, the second fluid (e.g., liquid) comprises at least one of a bicarbonate solution, sodium bicarbonate, hydrogen peroxide, carbonic acid, and potassium bicarbonate. In some embodiments, the source of foamed fluid generates the foamed fluid by mechanical agitation of a liquid. In some embodiments, the source of foamed fluid generates the foamed fluid by injecting gas into a liquid.

Some embodiments of the present wound-treatment apparatuses comprise: a drape for securing to the skin of a patient around a wound, thereby creating a space between the wound and the drape; a wound filler for placement on the wound in the space between the wound and the drape; a vacuum source in fluid communication with the space between the wound and the drape for applying a negative pressure to that space; and a source of liquid in fluid communication with the space between the wound; where the wound filler comprises a foaming agent for forming a foam when liquid from the liquid source contacts the foaming agent. In some embodiments, the foaming agent comprises one or more ingredients selected from the group consisting of: sodium bicarbonate, hydrogen peroxide, carbonic acid, and potassium bicarbonate.

Certain exemplary embodiments include a wound treatment method comprising: delivering a foamed fluid to a wound of a patient through a wound dressing covering the wound and coupled to skin around the wound. Particular embodiments comprise combining a first fluid (e.g., liquid) and a second fluid (e.g., liquid) to generate the foamed fluid. In certain embodiments, the first fluid (e.g., liquid) comprises an acidic solution, and the second fluid (e.g., liquid) comprises a basic solution. In particular embodiments, at least one of the first fluid (e.g., liquid) and the second fluid (e.g., liquid) comprises a surfactant configured to stabilize the foamed fluid. The first fluid (e.g., liquid) may comprise one or more ingredients selected from the group consisting of: citric acid, acetic acid, hypochlorous acid, ascorbic acid, benzoic acid, saline, and lactated Ringer's solution. The second fluid (e.g., liquid) may comprise one or more ingredients selected from the group consisting of: sodium bicarbonate, carbonic acid, sodium citrate, potassium citrate, potassium bicarbonate, potassium sulfate, disodium phosphate, and sodium hypochlorite. In particular embodiments, combining the first fluid (e.g., liquid) and the second fluid (e.g., liquid) comprises activating a first fluid source to deliver the first fluid and activating a second fluid source to deliver the second fluid.

In certain embodiments, the first fluid (e.g., liquid) and second fluid (e.g., liquid) are delivered to a combiner fitting to combine the first fluid and the second fluid to generate the foamed fluid prior to the foamed fluid being delivered to the wound dressing. In particular embodiments, the first fluid (e.g., liquid) and the second fluid (e.g., liquid) are delivered to the wound dressing such that the first fluid and the second fluid combine to generate the foamed fluid in the wound dressing.

Exemplary embodiments may include: activating a fluid source to deliver a fluid (e.g., liquid) to a foaming mechanism; and activating a foaming mechanism to foam the first fluid to generate the foamed fluid, where activating the fluid source and activating the foaming mechanism are performed prior to delivering the foamed fluid to the wound dressing. In particular embodiments, the foaming mechanism comprises a mechanical agitator. In certain embodiments, the mechanical agitator comprises one or more rotating elements. The foaming mechanism may comprise a gas injector in certain embodiments. In certain embodiments, the fluid (e.g., liquid) comprises one or more ingredients selected from the group consisting of: comprises sodium bicarbonate, citric acid, hydrogen peroxide, hypochlorous acid, sodium hypochlorite, sodium citrate, carbonic acid, potassium bicarbonate, potassium phosphate, and acetic acid.

In particular embodiments, a portion of the wound dressing is impregnated with a foaming agent configured to foam a first fluid (e.g., liquid), and where delivering a foamed fluid to a wound comprises delivering a first fluid to the wound dressing such that the first fluid reacts with the foaming agent to generate the foamed fluid. In certain embodiments, the foaming agent comprises one or more ingredients selected from the group consisting of: sodium bicarbonate, citric acid, hydrogen peroxide, hypochlorous acid, sodium hypochlorite, sodium citrate, carbonic acid, potassium bicarbonate, potassium phosphate, and acetic acid. In particular embodiments, the first fluid comprises an acidic solution. In certain embodiments, the first fluid comprises one or more ingredients selected from the group consisting of: citric acid, acetic acid, hypochlorous acid, ascorbic acid, benzoic acid, and lactated Ringer's solution.

In particular embodiments, the wound dressing comprises a drape coupled to the skin around the wound and a wound filler disposed between the drape and wound, and the wound filler is impregnated with the foaming agent. In certain embodiments, the foamed fluid includes gas comprising between 10 and 99 percent of the volume of the foamed fluid. In specific embodiments, the foamed fluid includes gas comprising between 20 and 90 percent of the volume of the foamed fluid. In particular embodiments, the foamed fluid includes gas comprising between 40 and 80 percent of the volume of the foamed fluid. In still more particular embodiments, the foamed fluid includes gas comprising between 60 and 75 percent of the volume of the foamed fluid.

Certain embodiments comprise applying negative pressure to the wound through the wound dressing. In particular embodiments, applying negative pressure comprises activating a vacuum source coupled to the wound dressing. In specific embodiments, applying negative pressure is performed after delivering the foamed fluid has stopped. In certain embodiments, applying negative pressure is performed simultaneously with delivering the foamed fluid.

Particular embodiments comprise a wound treatment apparatus comprising: a vacuum source; a first fluid source configured to deliver a first fluid (e.g., liquid); and a second fluid source configured to deliver a second fluid (e.g., liquid); where the apparatus is configured to be coupled to a wound dressing such that the first and second fluid sources are activatable to combine the first and second fluids to generate a foamed fluid and deliver the foamed fluid to a wound. Certain embodiments comprise a wound dressing configured to be coupled to skin around a wound of a patient such that the wound dressing covers the wound. In particular embodiments, the wound dressing comprises a drape configured to be coupled to the skin around a wound, and a wound filler configured to be disposed between the drape and the wound.

Certain embodiments include a wound treatment apparatus comprising: a vacuum source; a fluid source configured to deliver a fluid (e.g., liquid); and a foaming mechanism coupled to the fluid source and configured to foam the fluid, where the apparatus is configured to be coupled to a wound dressing such that the fluid source and foaming mechanism are activatable to deliver the foamed fluid to a wound. Specific embodiments comprise a wound dressing configured to be coupled to skin around a wound of a patient such that the wound dressing covers the wound. In certain embodiments, the wound dressing comprises a drape configured to be coupled to the skin around a wound of a patient and a wound filler configured to be disposed between the drape and the wound.

Particular embodiments include a wound treatment apparatus comprising: a vacuum source; and a fluid source configured to deliver a fluid (e.g., liquid), where the apparatus is configured to be coupled to a wound dressing such that the fluid source is activatable to deliver a foamed fluid to a wound. In certain embodiments, the wound dressing comprises a drape configured to be coupled to the skin around a wound of a patient and a wound filler configured to be disposed between the drape and the wound, where the wound filler is impregnated with the foaming agent. In specific embodiments, the wound filler comprises a sterile porous member. In certain embodiments, the foaming agent comprises one or more ingredients selected from the group consisting of: sodium bicarbonate, hydrogen peroxide, carbonic acid, and potassium bicarbonate.

Certain embodiments include a wound filler comprising: a sterile porous member impregnated with a foaming agent configured to foam a fluid (e.g., liquid), where the porous member is configured to be disposed between a wound of a patient and a drape coupled to skin around the wound such that the drape covers the wound filler and the wound.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a wound treatment method that "comprises," "has," "includes" or "contains" one or more steps possesses those one or more steps, but is not limited to possessing only those one or more steps. Likewise, a wound treatment system that "comprises," "has," "includes" or "contains" one or more elements possesses those one or more elements, but is not limited to possessing only those elements.

Further, a device, apparatus or structure that is configured in a certain way is configured in at least that way, but it can also be configured in other ways than those specifically described.

Figure 1:
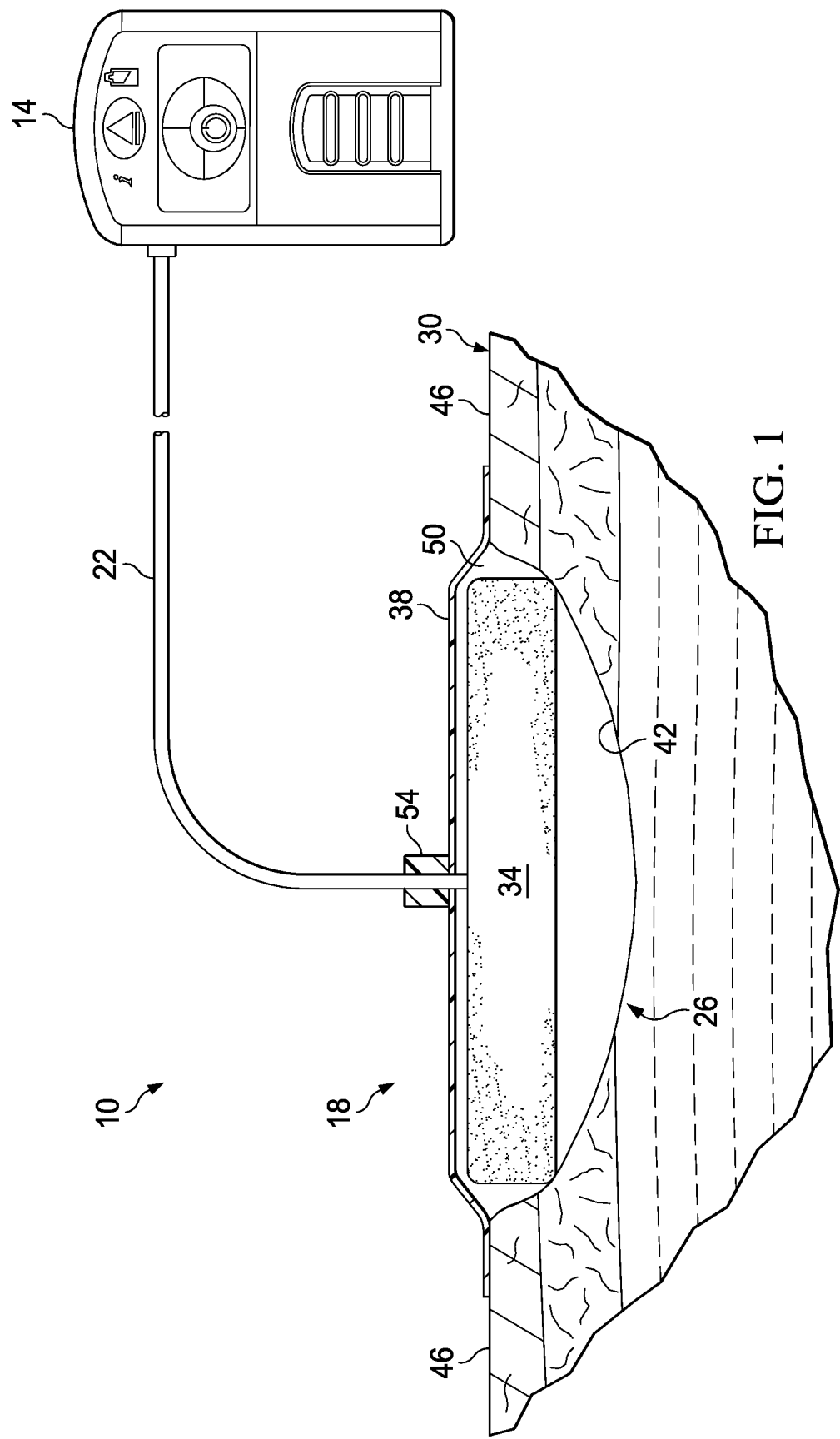
FIG. 1 depicts a side view of an exemplary embodiment of a wound treatment system according to the present disclosure.

Referring now to the drawings, and more particularly to FIG. 1, shown therein is an embodiment of one of the present wound treatment system 10. In the embodiment shown, system 10 comprises a wound-treatment apparatus 14, and a wound dressing 18. In the embodiment shown, apparatus 14 is coupled to wound dressing 18 by a conduit 22. As shown, dressing 18 is configured to be coupled to (and is shown coupled to) a wound 26 of a patient 30. More particularly, in the embodiment shown, dressing 18 comprises a wound insert 34 and a drape 38. As shown, wound insert 34 is configured to be positioned (and is shown positioned) on wound 26 (e.g., on or adjacent to wound surface 42), and/or drape 38 is configured to be coupled to (and is shown coupled to) skin 46 of the patient adjacent to wound 26 such that drape 38 covers wound insert 34 and wound 26, and forms a chamber 50 between drape 38 and wound 26 (e.g., wound surface 42).

Apparatus 14 can comprise, for example, a vacuum source configured to be actuatable (and/or actuated) to apply negative pressure (e.g., via conduit 22) to wound dressing 18, a fluid source configured to be actuatable (and/or actuated) to deliver (e.g., via conduit 22) a fluid (e.g., an installation fluid such as a medicinal fluid, antibacterial fluid, irrigation fluid, and/or the like) to wound dressing 18. System 10 can be implemented and/or actuated and/or coupled to patient 30 in any of various configurations and/or methods similar to those described in the prior art, including for example U.S. Pat. No. 7,611,500, the disclosure of which is incorporated here in its entirety. Additionally, various wound therapy systems and components are commercially available through and/or from KCI USA, Inc. of San Antonio, Texas, U.S.A. and/or its subsidiary companies such as in its V.A.C.® and SensaTRAC® product lines, as discussed further below.

Conduit 22 can comprise a single lumen conduit (e.g., switched between a vacuum source and/or a fluid source and apparatus 14), or can comprise multiple single-lumen conduits or a multi-lumen conduit such that, for example, fluid can be delivered and/or negative pressure can be applied to wound dressing 18 individually and/or simultaneously. Additionally, conduit 22 can comprise, for example, a first lumen for the application of negative pressure and/or fluid delivery, and at least one additional lumen for coupling to pressure sensor(s) to sense pressure or negative pressure between drape 38 and surface 42. In some embodiments, conduit 22 can comprise multiple lumens (e.g., as in a single conduit with a central lumen for application of negative pressure and/or fluid delivery, and one or more peripheral lumens disposed adjacent or around the central lumen such that the peripheral lumens can be coupled to a pressure sensor to sense a pressure or negative pressure between drape 38 and surface 42 (e.g. in space 50). The lumens may be arranged with a central lumen and other lumens disposed radially around the central lumen, or in other suitable arrangements. The lumens may also be provided in separate conduits. In the embodiment shown, system 10 further comprises a wound dressing connection pad 54 configured to be coupled (and is shown coupled) to conduit 22. One example of a suitable connection pad 54 is the "V.A.C. T.R.A.C.® Pad," commercially available from KCI. One example of a suitable drape 38 includes the "V.A.C.® Drape" commercially available from KCI. Another example of a connection pad 54 is disclosed in U.S. patent application Ser. No. 11/702,822, incorporated above.

One example of a suitable drape 38 includes the "V.A.C.® Drape" commercially available from KCI USA, Inc. (and its affiliates) of San Antonio, Texas, U.S.A.

Typical open-celled foam wound fillers generally do not wick or distribute fluids effectively. An effective wicking wound filler is desirable where fluids are instilled into a wound for various therapeutic effects (e.g., antiseptics and antibiotics). By reducing the pore size of such foams (and also by incorporating hydrophilic coatings, or using inherently hydrophilic foams), the wicking ability may be improved, but smaller pores can attract the risk of increased blocking by wound fluid borne agents and particulates. Utilizing voids (e.g., holes or channels) in the foam can help to reduce the effects of poor manifolding due to pore blocking, but current processes limit the length of void that may be created in the foam.

Exemplary embodiments of the present disclosure may utilize wound insert 34 comprising an open-celled foam (which may also be reticulated) that is configured to exhibit hydrophilic properties. In contrast to hydrophobic foams traditionally used with NPWT systems and methods, the hydrophilic properties of wound insert 34 improve the movement of fluids (e.g., liquids, such as, instillation fluids, body fluids, exudate, and the like) through the wound insert, such that fluid is encouraged to travel through wound insert 34 rather than around the wound insert 34 or adjacent to the interface between drape 38 and skin 46.

With traditional hydrophobic wound inserts, fluid typically travels in a path such that the fluid minimizes contact with the foam, and such that fluid is repelled from the foam and may generate pressure between the foam and interface between drape 38 and skin 46. In this way with hydrophobic wound inserts, drape 38 may be forced away from skin 46 about the perimeter of wound 26. In this way, with traditional hydrophobic wound inserts, very little of the fluid is retained or transferred through the foam itself. Because fluid may be forced outward from the hydrophobic wound insert, the fluid can generate a positive pressure at the interface between the drape and skin adjacent to the wound. This can lead to a ballooning effect which can stress the interface between drape adjacent skin, and can lead to failure of the adhesive generally used to couple the drape to the skin.

However, with hydrophilic wound inserts 34, fluid can travel through the wound insert 34 (e.g., evenly dispersed throughout wound insert 34), thus decreasing the positive pressure within chamber 50 and at the interface between drape 38 and skin 46. As such, with hydrophilic wound inserts 34, fluid typically will not pool at the interface between drape 38 and skin 46 as quickly, such that the integrity of adhesive or the like coupling drape 38 to skin 46 is maintained longer and permits more durable adhesion between drape 38 and 46. In this way, wound dressings 18 comprising drape 38 and wound insert 34 are typically more durable and/or less prone to failure.

As illustrated in the exemplary embodiment of FIG. 1, wound dressings 18 comprise a wound insert 34 configured to be positioned on a wound 26 (e.g., wound surface 42) of a patient (e.g., 30), the wound insert comprising an open-celled foam (which may also be reticulated) configured to exhibit hydrophilic properties; and a drape 38 configured to be coupled to skin 46 of the patient adjacent the wound such that drape 38 covers wound insert 34 and wound 26 and forms chamber 50 between the drape and the wound. Wound insert 34 can comprise any suitable material and/or combination of materials that permit wound insert 34 to exhibit hydrophilic properties. For example, in some embodiments, wound insert 34 comprises an open celled hydrophobic foam (which may also be reticulated) that is coated with a hydrophilic coating (e.g., a coating configured to cause the hydrophobic foam to exhibit hydrophilic properties). In some embodiments, the hydrophilic coating comprises polyvinyl alcohol (PVOH), plasticizer (e.g., triethyl citrate, or the like), hydrophilic polyurethane, gelatin, hyaluronic acid, heparin, and/or any suitable coating configured to cause the coated hydrophobic foam to exhibit hydrophilic properties.

Figure 2:
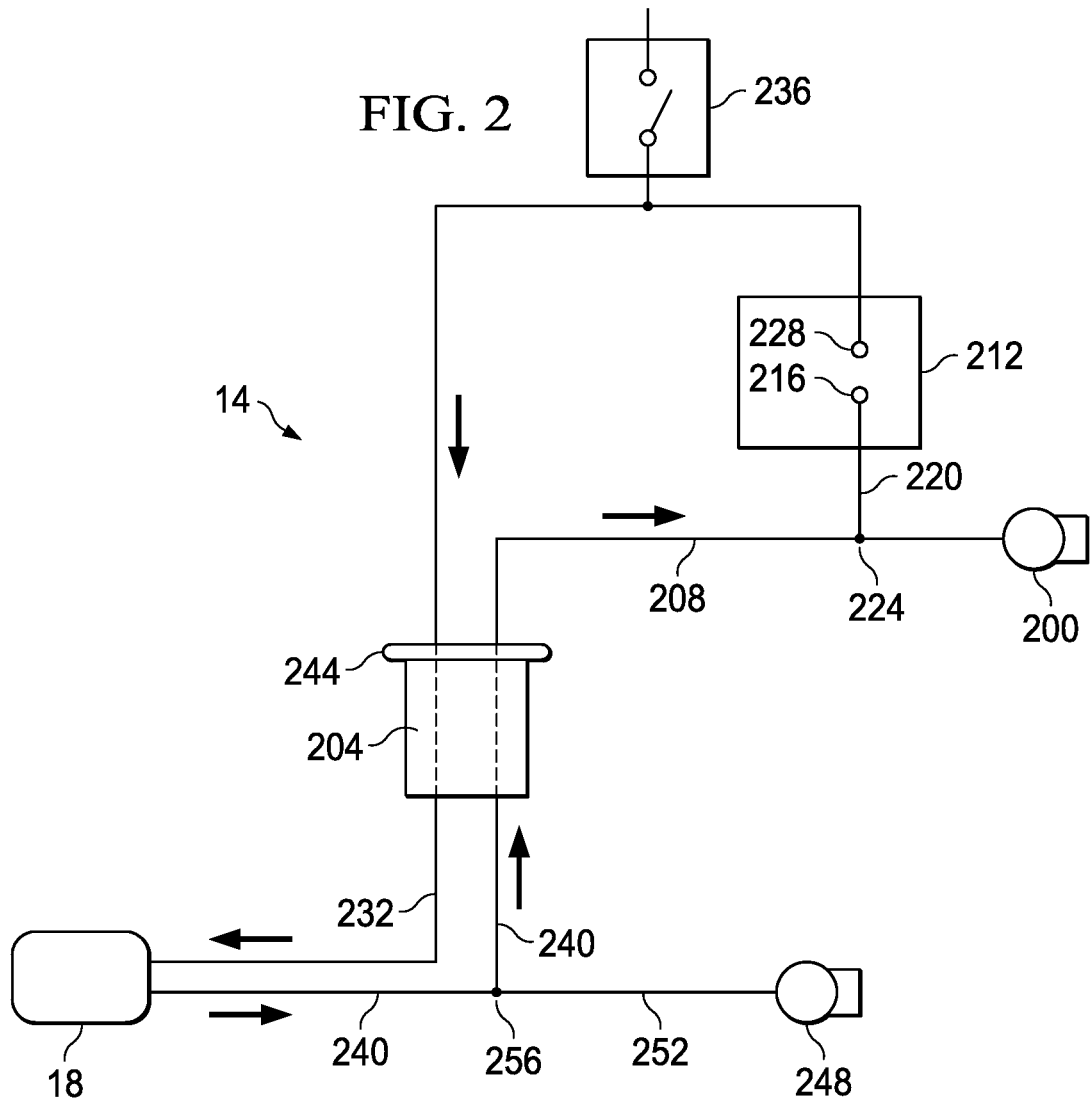
FIG. 2 depicts a schematic block diagram of a first exemplary embodiment of a wound treatment system according to the present disclosure.

Embodiments of the present wound treatment methods may be better understood with reference to FIG. 2. FIG. 2 depicts a schematic block diagram of one embodiment of system 10. In the embodiment shown, wound dressing 18 is coupled to apparatus 14, and apparatus 14 comprises a vacuum source 200 (e.g., a vacuum pump and/or the like) coupled to a canister 204 (e.g., configured to receive exudate and or the like from wound dressing 18) by way of a conduit 208. In the embodiment shown, apparatus 14 further comprises: a pressure sensor 212 having a first pressure transducer 216 coupled to conduit 208 by way of conduit 220 and/or tee-fitting 224, and a second pressure transducer 228 coupled to canister 204 and/or wound dressing 18 by way of conduit 232. Pressure sensor 212 is configured to sense the negative pressure in wound dressing 18, and/or any of the various lumens (e.g., within conduits) coupled to wound dressing 18, pressure sensor 212, and/or vacuum source 200.

In the embodiment shown, apparatus 14 further comprises a pressure release valve 236 coupled to conduit 232. Further, in the embodiment shown, canister 204 and vacuum source 200 are coupled to wound dressing 18 by way of conduit 240. In the embodiment shown canister 204 can comprise a filter 244 at or near an outlet of canister 204 to prevent liquid or solid particles from entering conduit 208. Filter 244 can comprise, for example, a bacterial filter that is hydrophobic and/or lipophilic such that aqueous and/or oily liquids will bead on the surface of the filter. Apparatus 14 is typically configured such that during operation vacuum source 200 will provide sufficient airflow through filter 244 that the pressure drop across filter 244 is not substantial (e.g., such that the pressure drop will not substantially interfere with the application of negative pressure from wound dressing 18 from vacuum source 200).

In the embodiment shown, apparatus 14 further comprises a fluid source 248 coupled to wound dressing 18 by way of a conduit 252 that is coupled to conduit 240 such as, for example, by way of a tee- or other suitable fitting 256. In some embodiments, tee fitting 256 can comprise a switch valve and the like such that communication can be selectively permitted between wound dressing 18 and vacuum source 200, or between wound dressing 18 and fluid source 248. In some embodiments apparatus 14 comprises only one of vacuum source 200 and fluid source 248. For embodiments of apparatus 14 that comprise only fluid source 248, canister 204 and/or pressure sensor 212 can also be omitted. In various embodiments, such as the one shown, conduit 232 and/or conduit 240 and/or conduit 252 can be combined and/or comprised in a single multi-lumen conduit, such as is described above with reference to FIG. 1.

In various embodiments, such as the one shown in FIG. 2, apparatus 14 can be configured such that as soon as the liquid in the canister reaches a level where filter 244 is occluded, a much-increased negative (or subatmospheric) pressure occurs in conduit 208 and is sensed by transducer 216. Transducer 216 can be connected to circuitry that interprets such a pressure change as a filled canister and signals this by means of a message on a visible and/or audible alarm that canister 204 requires emptying and/or replacement, and/or that automatically shuts off or disables vacuum source 200.

Apparatus 14 can also be configured to apply negative (or subatmospheric) pressure (e.g., continuously, intermittently, and/or periodically) to the wound site, and/or such that pressure relief valve 236 enables pressure at the wound site to be brought to atmospheric pressure rapidly. Thus, if apparatus 14 is programmed, for example, to relieve pressure at ten-minute intervals, at these intervals pressure relief valve 236 can open for a specified period, allow the pressure to equalize at the wound site, and then close to restore the negative pressure. It will be appreciated that when constant negative pressure is being applied to the wound site, valve 236 remains closed to prevent leakage to or from atmosphere. In this state, it is possible to maintain negative pressure at the wound site without running and/or operating pump 200 continuously, but only from time to time or periodically, to maintain a desired level of negative pressure (i.e. a desired pressure below atmospheric pressure), which is sensed by transducer 216. This saves power and enables the appliance to operate for long periods on its battery power supply.

Figure 3:
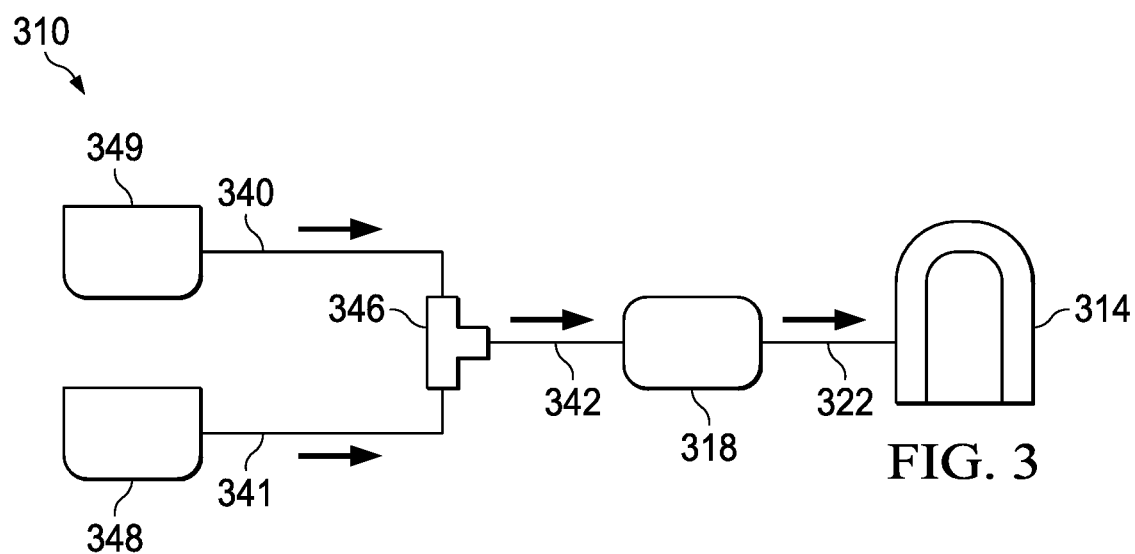
FIG. 3 depicts a schematic block diagram of a second exemplary embodiment of a wound treatment system according to the present disclosure.

In specific embodiments, the fluid provided to a wound dressing may comprise a foamed fluid. Referring now to FIG. 3, a schematic diagram of a wound treatment system 310 comprises a wound dressing 318 and a wound treatment apparatus 314 coupled via a conduit 322. Similar to previously-described embodiments, apparatus 314 may comprise a vacuum source configured to apply intermittent negative (or subatmospheric) pressure to the wound dressing 318. In this exemplary embodiment, a first fluid source 348 comprising a first fluid and a second fluid source 349 comprising a second fluid are coupled to wound dressing 318 via conduits 340, 341, 342 and coupling member or combiner fitting 346. In exemplary embodiments, first and second fluids from first fluid source 348 and second fluid source 349 are configured to produce a foamed fluid when mixed. In related exemplary embodiments, first and second fluids from first and second fluid sources 348, 349 are delivered separately to wound dressing 318 and mixed within wound dressing 318 to produce a foamed fluid. In certain embodiments, first fluid source 348 may comprise a first fluid that is an acidic solution, while second fluid source 349 may comprise a second fluid that is a basic solution.

In specific exemplary embodiments, first fluid source 348 may comprise citric acid, acetic acid, hypochlorous acid, ascorbic acid, and/or benzoic acid. Second fluid source 349, in exemplary embodiments, may comprise a basic or bicarbonate solution. Non-limiting examples of a second fluid from second fluid source 349 include sodium bicarbonate, hydrogen peroxide and carbonic acid. In particular exemplary embodiments, the first and/or second fluids may comprise a surfactant configured to stabilize the foamed fluid. In exemplary embodiments, the foamed fluid includes gas comprising between 10 and 99 percent (e.g., between 20 and 90, and/or between 40 and 80 percent) of the volume of the foamed fluid. For example, in some embodiments, the foamed fluid includes gas comprising between 60 and 75 percent of the volume of the foamed fluid such that the foamed fluid contains substantially less liquid than a fluid comprising only liquid, but still contains enough liquid to be effective for cleaning, debriding, and/or disinfecting a wound.

During operation of wound treatment system 310, first fluid source 348 and second fluid source 349 can be activated to deliver first and second fluids, respectively, that are drawn into conduit 342 and mixed together to produce a foamed fluid that enters wound dressing 318. In specific exemplary embodiments, wound dressing 318 may be vented to allow excess gas to escape (e.g., by opening pressure-relief valve 236, or by providing a one-way valve in drape 38).

Delivering a foamed instilled fluid can increase its coverage in the wound by reducing the amount of fluid required to fill the wound and wound dressing 318. In particular embodiments, wound dressing 318 may comprise distribution channels to distribute the foamed fluid to particular regions. Although the foamed instill fluid is effectively diluted with gas, as the foam collapses at the wound surface the result is efficient coverage, particularly where surfactants are used.

In certain embodiments, the use of foamed fluid can provide additional versatility for the frequency and/or duration of the liquid instillation. For example, more frequent fluid instills, or even a continuous instillation, may be employed to present successive waves of foam to the wound surface without increasing the total volume of instillation fluid (as compared to methods using non-foamed liquids).

In certain exemplary embodiments, the foam is self-supporting and will rapidly collapse under the application of negative pressure. In other embodiments, the foam is substantially stable (will resist collapsing) under the application of negative pressure for at least a period of time sufficient to draw foam into a wound dressing by application of negative pressure without collapsing the foam. The compressible nature of the foam can allow slight overfilling of the wound without placing undue pressure on the dressing, which can reduce the occurrence of leaks. The application of a vacuum during instillation, the compressible nature of the foam, and/or the use of suitable surfactants can enable the foamed fluid to more effectively fill tortuous cavities (as compared to non-foamed fluids). Although high volumes of foamed fluid may be used to instill a wound, the foamed fluid can be withdrawn to a canister (and collapsed, if not collapsed in or as drawn from the wound), thereby reducing the volume of used liquid (e.g., which must be disposed of).

Figure 4:
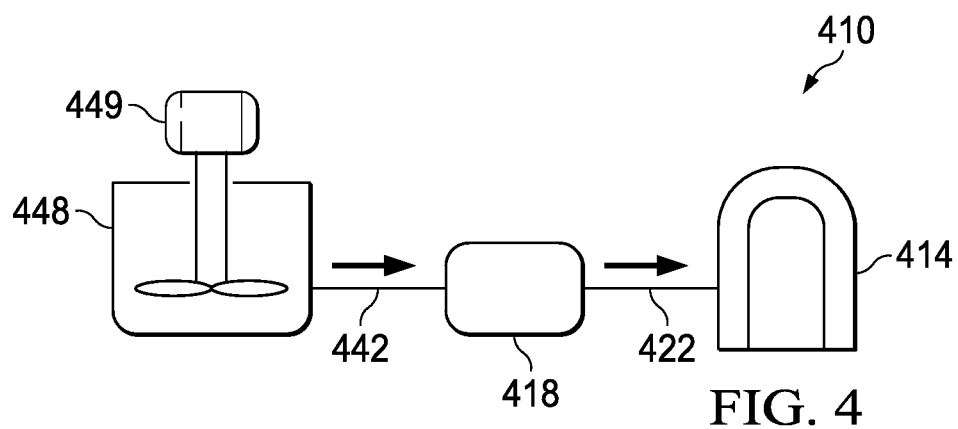
FIG. 4 depicts a schematic block diagram of a third exemplary embodiment of a wound treatment system according to the present disclosure.

In other embodiments, foamed instillation fluid may be generated via a mechanical apparatus. Referring now to FIG. 4, a wound treatment system 410 comprises a wound dressing 418 and a wound treatment apparatus 414 coupled via a conduit 422. Similar to previously-described embodiments, apparatus 414 may comprise a vacuum source configured to apply intermittent negative (or subatmospheric) pressure to the wound dressing 418. In this exemplary embodiment, a first fluid source 448 comprising a first fluid is coupled to wound dressing 418 via a conduit 442. In the exemplary embodiment shown, a foaming mechanism 449 (e.g. a mechanical agitator), is used to generate a foamed fluid from the first fluid (e.g., liquid), which can be instilled into wound dressing 418 as previously described. In particular exemplary embodiments foaming mechanism 449 may comprise one or more rotating elements that generate a foam when placed in contact with the first fluid. In specific exemplary embodiments, foaming mechanism 449 may comprise an electric motor configured to rotate a shaft with paddles or other shaft extensions that contact the first fluid during operation.

Figure 5:
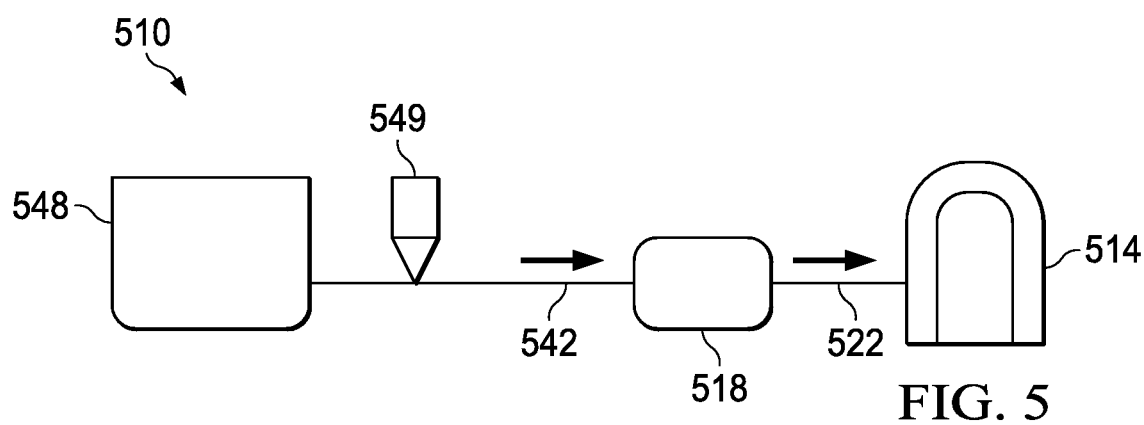
FIG. 5 depicts a schematic block diagram of a fourth exemplary embodiment of a wound treatment system according to the present disclosure.

In still other embodiments, foamed instillation fluid may be generated via a different foaming mechanism. Referring now to FIG. 5, a wound treatment system 510 comprises a wound dressing 518 and a wound treatment apparatus 514 coupled via a conduit 522. Similar to previously-described embodiments, apparatus 514 may comprise a vacuum source configured to apply intermittent negative (or subatmospheric) pressure to the wound dressing 518. In this exemplary embodiment, a first fluid source 548 comprising a first fluid is coupled to wound dressing 518 via a conduit 542. In the illustrated exemplary embodiment, a foaming mechanism 549 (e.g. a gas injector) is used to inject a gas into the first fluid (e.g., liquid) and generate a foamed fluid that can be instilled into wound dressing 518 as previously described. In specific exemplary embodiments, foaming mechanism 549 may comprise a reservoir of pressurized air and a nozzle configured to direct the pressurized air into the first fluid.

Still other embodiments may comprise different methods or systems for generating a foamed instill fluid. For example, instead of reactive liquids or mechanically generated foam, certain embodiments may use low boiling point liquids, emulsions, or dispersions that may be delivered to a wound and generate foam upon an increase in temperature. For example, in some embodiments, a low-boiling-point liquid is added another liquid (e.g., water, saline, etc.) such that upon boiling, the low-boiling-point liquid will foam the other liquid. In certain exemplary embodiments, an increase in temperature sufficient to cause boiling of the low-boiling-point liquid can be supplied by the body temperature of the patient. In other exemplary embodiments, the increase in temperature may be provided by an external heater.

In particular exemplary embodiments, the wound dressing may act as a catalyst on given instilled liquids generating gases and/or create foamed liquids. For example, certain metals on contact with peroxides and hydroperoxides will liberate oxygen. Similar processes may be employed to liberate other gases such as carbon dioxide for example. In certain embodiments, the wound dressing may comprise or be coated with a foaming agent that when exposed to a dilute acid will liberate a gas (e.g., carbon dioxide). In certain embodiments, the foaming agent may comprise sodium bicarbonate, potassium bicarbonate, and carbonic acid.

In particular embodiments, the wound dressing comprises a drape coupled to the skin around the wound and a wound filler disposed between the drape and wound, and the wound filler can be impregnated with the foaming agent.

In particular embodiments, the gas generated may be a wound disinfecting agent (e.g., an antibiotic or antiseptic). In certain exemplary embodiments, abrasive particulates may be added to the foam to provide a scouring effect and help debride the wound.

Particular exemplary embodiments utilize closed-cell foams that produce little or no granulation under NPWT, such as, for example, alone or in combination with open-cell foams. This low or no granulation effect may be employed in wounds were metal components (e.g. bolts, plates, etc.) are employed and granulation is not desired. This can protect the metal components from the granulation process by applying foam to them, such that, for example, the closed-cell foam directs fluids (e.g., foamed fluids) around the closed-cell foam to be applied to the wound around such metal components. In exemplary embodiments, the foam can more efficiently cover these metal structures than typical methods that use films or gels.

Exemplary embodiments also comprise wound treatment methods utilizing the previously-described systems. In specific exemplary embodiments, the foamed fluid is generated (e.g., by one or more of the previously described methods or systems) and delivered to a wound of a patient through a wound dressing that is coupled to the skin around the wound.

The various illustrative embodiments of devices, systems, and methods described herein are not intended to be limited to the particular forms disclosed. Rather, they include all modifications, equivalents, and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

It will be understood that the benefits and advantages described above may relate to one embodiment or may relate to several embodiments. It will further be understood that reference to 'an' item refers to one or more of those items, unless otherwise specified.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the scope of this invention.

We claim:

1. A system for treating a tissue site, comprising:
   a foam member configured to be disposed at the tissue site;
   a drape configured to be disposed over the foam member to form a space;
   a first fluid source configured to provide a first fluid to the space; and
   a second fluid source configured to provide a second fluid to the space;
   wherein the first fluid is configured to combine with the second fluid to provide a foamed fluid to the space.

2. The system of claim 1, wherein the first fluid is configured to combine with the second fluid at the space to form the foamed fluid.

3. The system of claim 1, wherein the first fluid source is configured to provide the first fluid to the space before the second fluid source provides the second fluid to the space.

4. The system of claim 1, wherein the first fluid source is fluidly coupled to a combiner, and the second fluid source is fluidly coupled to the combiner.

5. The system of claim 4, wherein the combiner is fluidly coupled to the space.

6. The system of claim 5, wherein the first fluid is configured to combine with the second fluid to form the foamed fluid before the foamed fluid reaches the space.

7. The system of claim 5, wherein the first fluid is configured to combine with the second fluid at the combiner to form the foamed fluid.

8. The system of claim 5, wherein the combiner is fluidly coupled to the space via a conduit.

9. The system of claim 8, wherein the first fluid is configured to combine with the second fluid in the conduit.

10. The system of claim 1, further comprising a negative pressure source configured to apply a negative pressure to the space.

11. The system of claim 1, wherein the first fluid is acidic.

12. The system of claim 1, wherein the first fluid comprises at least one of citric acid, acetic acid, hypochlorous acid, ascorbic acid, and benzoic acid.

13. The system of claim 1, wherein the second fluid is basic.

14. The system of claim 1, wherein the second fluid comprises a bicarbonate solution.

15. The system of claim 1, wherein the second fluid comprises at least one of sodium bicarbonate, hydrogen peroxide, and potassium bicarbonate.

16. The system of claim 1, wherein the foam member further comprises abrasive particulates.

17. A method for treating a wound, comprising:
    providing a foam member to the wound;
    disposing a drape over the foam member to form a space;
    providing a first fluid to the space; and providing a second fluid to the space;
wherein the first fluid and the second fluid are configured to combine to form a foamed fluid at the space.

* * * * *